United States Patent [19]

Reed et al.

[11] 4,236,406
[45] Dec. 2, 1980

[54] METHOD AND APPARATUS FOR SONIC VELOCITY TYPE WATER CUT MEASUREMENT

[75] Inventors: Philip W. Reed; John D. Alexander, both of Ponca City, Okla.

[73] Assignee: Conoco, Inc., Ponca City, Okla.

[21] Appl. No.: 967,938

[22] Filed: Dec. 11, 1978

[51] Int. Cl.³ .......................................... G01N 29/02
[52] U.S. Cl. .................................... 73/61.1 R; 73/597; 73/861.04; 73/861.27
[58] Field of Search ................ 73/61.1 R, 194 A, 200, 73/597

[56] References Cited

U.S. PATENT DOCUMENTS

| Re. 28,929 | 8/1976 | Brown . | |
|---|---|---|---|
| 2,987,366 | 6/1961 | Meyers | 73/200 X |
| 3,171,095 | 2/1965 | Gennari . | |
| 3,290,934 | 12/1966 | Brown et al. | |
| 3,697,936 | 10/1972 | Zacharias, Jr. et al. | |
| 3,710,615 | 1/1973 | Johnson et al. | 73/61 R |
| 3,890,423 | 6/1975 | Zacharias, Jr. | |
| 3,973,430 | 8/1976 | Cirulis et al. | |
| 4,032,259 | 6/1977 | Brown | 73/194 A X |
| 4,080,837 | 3/1978 | Alexander et al. | |

FOREIGN PATENT DOCUMENTS 551509  5/1977  U.S.S.R. ................................ 73/194 A

OTHER PUBLICATIONS

W. R. Loosemore, et al., "A New Ultrasonic Flowmeter", *Ultrasonics,* Jan. 1969, pp. 43-46.
E. M. Zacharias, Jr., "Process Measurements by Sound Velocimetrs", *Instruments and Control Systems,* Sep. 1970, pp. 112-113.

*Primary Examiner*—Charles A. Ruehl
*Attorney, Agent, or Firm*—A. Joe Reinert

[57] ABSTRACT

In a method and apparatus for metering water content in an oil-water system by determining sonic velocities in the flowing oil-water mixture, and thereafter determining flow rate to provide individual oil and water rates which may then be integrated to provide oil and water volume of flow, the improvement comprising self-calibrating for salt content of the system water by measuring the speed of sound in the water phase only and utilizing the measured value in determinations of the system water cut.

14 Claims, 6 Drawing Figures

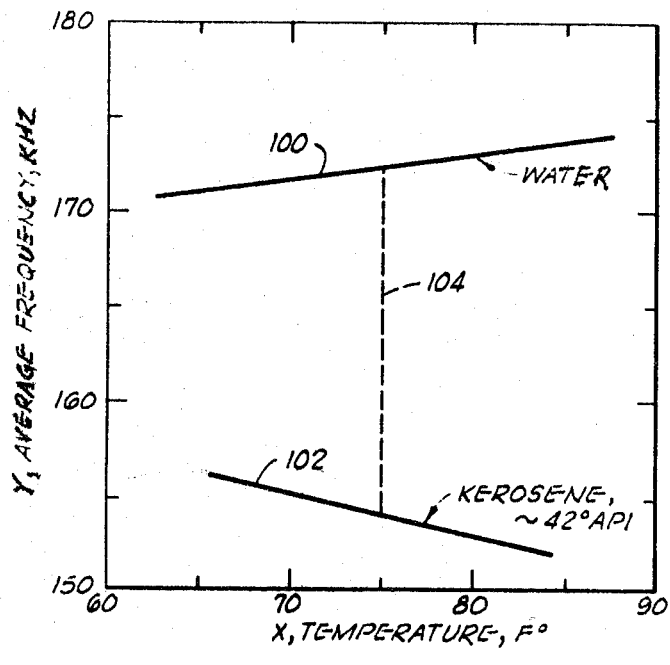
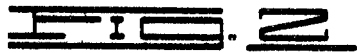
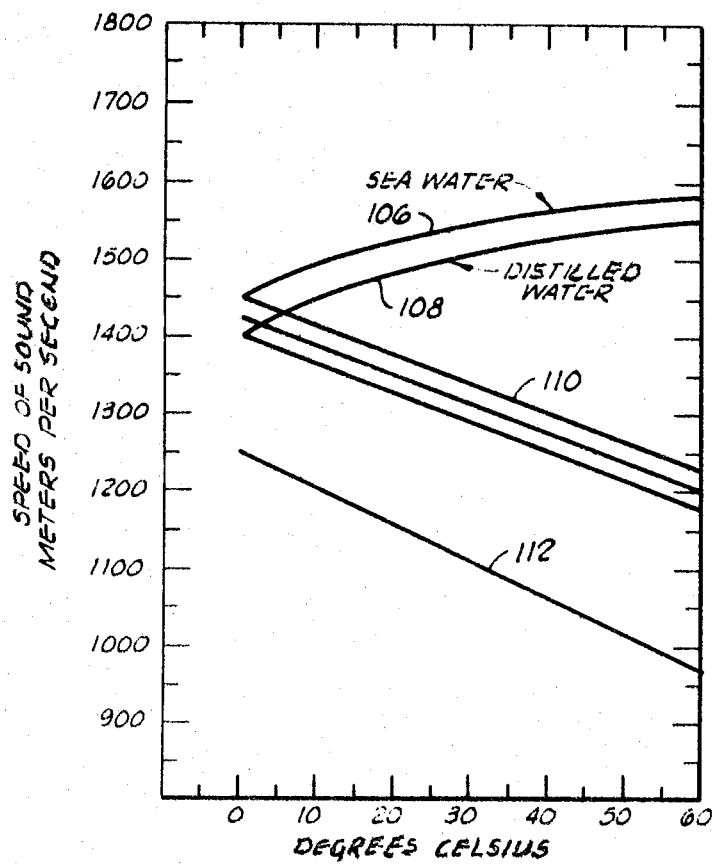
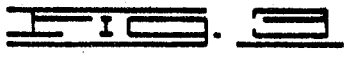

METHOD AND APPARATUS FOR SONIC VELOCITY TYPE WATER CUT MEASUREMENT

BACKGROUND OF THE INVENTION

1. Field of the Invention

The present invention relates to an improved method and apparatus for maintaining continual readout of the components of flowing oil-water systems thereby to record continual quantitative record.

2. Description of the Prior Art

The prior art includes several types of flow monitoring apparatus which have been utilized in the past for determining the content of oil and water in production oil well testing procedures and related pipeline transportation wherein oil-water systems are flowing. The prior methods utilize net oil computers or a related type of net oil analyzer which determines oil and water rates during well testing by utilizing two or three phase separators with subsequent analysis using a capacitance cell. Normally, a capacitance cell is only capable of measuring water content up to about 30%, and still further limitations of use are imposed by the degree of continuity of oil present in the system. Capacitance cell output is inherently non-linear and, when other factors contribute, high water contents of 50% and over are difficult to measure with any accuracy. A most recent improvement in methods for monitoring flow in oil-water systems is the subject matter of U.S. Pat. No. 4,080,837 issued Mar. 28, 1978 in the name of Alexander et al. and entitled "Sonic Measurement of Flow Rate and Water Content or Oil-Water Streams". The present subject matter constitutes an improvement on the above-identified teachings through improvement of the method and apparatus to enable self-calibration by directly determining the velocity of sound of the water phase of an oil-water mixture periodically as required to maintain accurate data readout.

SUMMARY OF THE INVENTION

The present invention contemplates a method and apparatus for determining content data relative to the flowing oil-water system wherein the water phase of the flowing mixture is separately tested by sonic flowmeter to derive a more accurate water sonic velocity for use in final determination of the flow rate and water content of the flowing oil-water system. There is provided in a sonic velocity type of oil-water metering system, provision for separately testing sonic velocity in water only in said system with application of such sonic velocity data as a self-calibrating input to the device producing readout of individual oil and water flow data. The oil-water system water sonic velocity is periodically determined as required and input to the data determining stages thereby to maintain greater accuracy of the water cut determination and to accommodate any changes in the composition of water present in the flowing system.

Therefore, it is an object of the present invention to provide a water cut measurement instrument of the sonic velocity type that is self-calibrating and capable of accommodating changes in composition of water present in the system.

It is also an object of the invention to provide a water cut measurement instrument having greater overall accuracy and, consequently, a greater number of useful applications.

Finally, it is an object of the present invention to provide means for actually separating and measuring sonic velocity of water that flows in an oil-water system.

Other objects and advantages of the invention will be evident from the following detailed description when read in conjunction with the accompanying drawings which illustrate the invention.

BRIEF DESCRIPTION OF THE DRAWINGS

FIG. 2 is a graph depicting frequency variation versus temperature for separate phases of water and kerosene;

FIG. 3 is a graph of speed of sound versus temperature illustrating the various values for particular oil and water substances;

DETAILED DESCRIPTION OF THE INVENTION

As fully described in U.S. Pat. No. 4,080,837, the water content of an oil-water mixture can be determined by the velocity of sound in the oil-water mixture. A complication is that the velocity of sound in water varies with the composition of the water. Produced waters from oil fields may have varying salt contents such that in certain situations there could be a material reduction in the accuracy of the water cut determination using the sonic velocity method. This difficulty may be lessened by providing in the sonic velocity measurement apparatus a means or procedure for measurement of the velocity of sound in the water actually present in the flowing mixture; and then using the water portion sonic velocity data in the calculations required to obtain water cut from the velocity of sound in the oil-water mixture. Thus, the apparatus becomes self-calibrating as to the water phase data thereby to lessen some inaccuracies that have resulted in certain usages.

A limit to the application of sonic-type water cut calculations was that the speed of sound in water will vary with the salt content of the water. The variation of 5000 ppm of salt can change the sonic velocity by 5.7 meters per second. In normal field operations such differences can occur from several sources. Wells producing from different formations may produce to the same battery and test systems and the waters from different formations have different compositions. Second, in water flood operations, where high water cut production frequently occurs and where sonic-type water cut instruments would be particularly useful, the injection water and the original formation water are seldom the same. Some wells are usually producing mostly original formation brine while others produce a high percentage of the injected water. Thus, each well will have a different water composition and this will also change with time. Still other causes of water changes are possible in the various situations.

A sonic-type flowmeter such as that of U.S. Pat. No. 4,080,837 can be made self-calibrating by having it measure the speed of sound of that water actually flowing in the system, and thereafter to use this measured value in the calculation of water cut, i.e., measurement utilizing the speed of sound through the oil-water mixture. Speed of sound in water and in oil, or more exactly the curve expressing speed of sound relative to the temperature in each fluid is required as the basis for the water cut calculation. These data are normally entered as constants in calibrating the flowmeter, and the meter will include an electronic microprocessor to make the necessary calculations and provide adjustment of the water curve to a measured point as it is periodically sampled.

Figure 1:
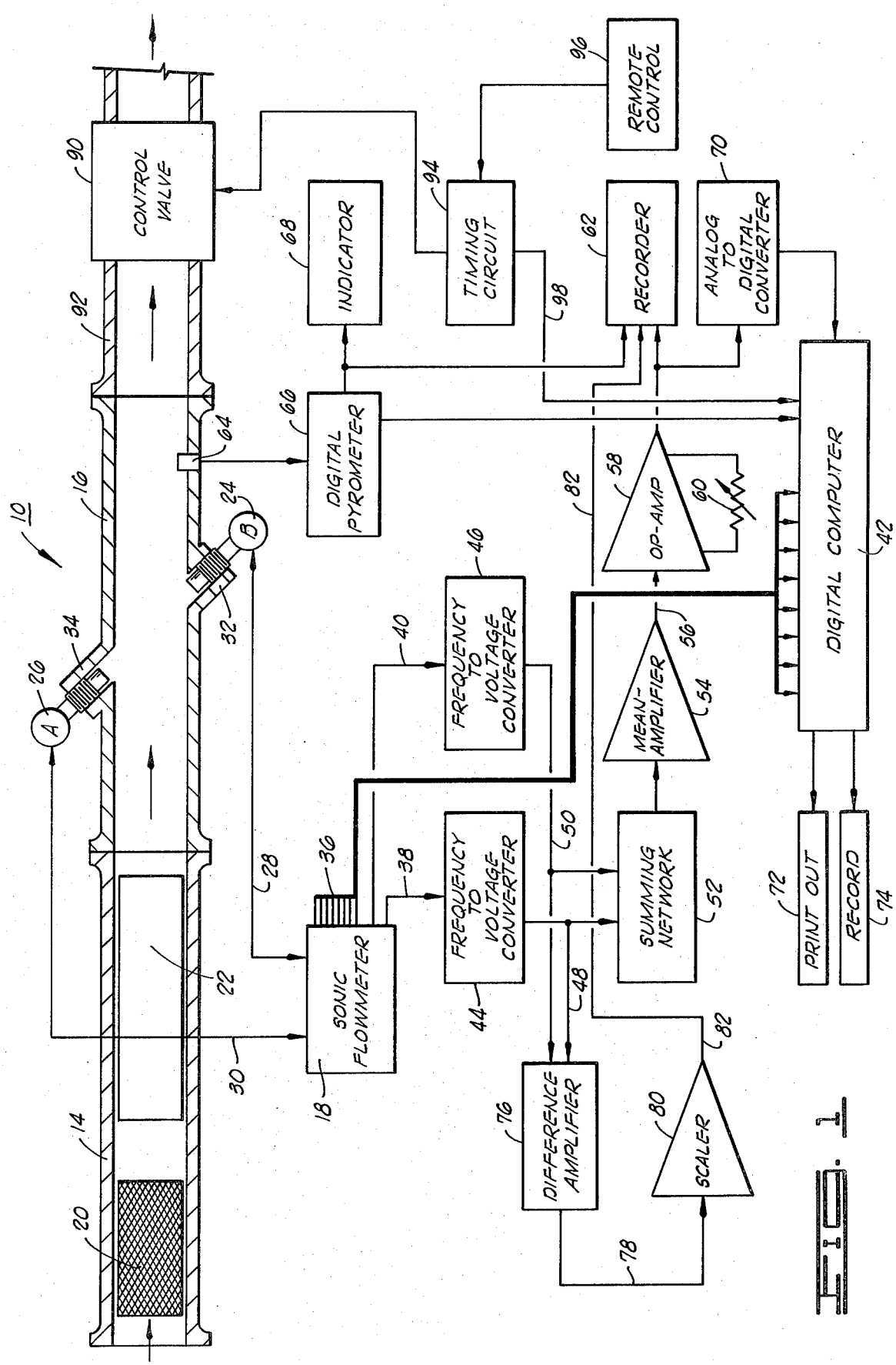
FIG. 1 is a schematic representation in partial block form which illustrates the present invention.

FIG. 1 illustrates a flowmeter for an oil-water system of the type that is more particularly described in U.S. Pat. No. 4,080,837, but with additional control structure that enables flow control for separation and sampling of water alone at periodic intervals, as necessitated. A measurement cell 10 is adapted to carry a mixture of crude oil and water 12, or water alone as controlled, as may be found at an oil well production site. A pipe section 14, which may include a mixing structure, is placed in the flow system just prior to metering section 16 which includes sensing and transducer devices for a sonic flowmeter 18.

Figure 6:
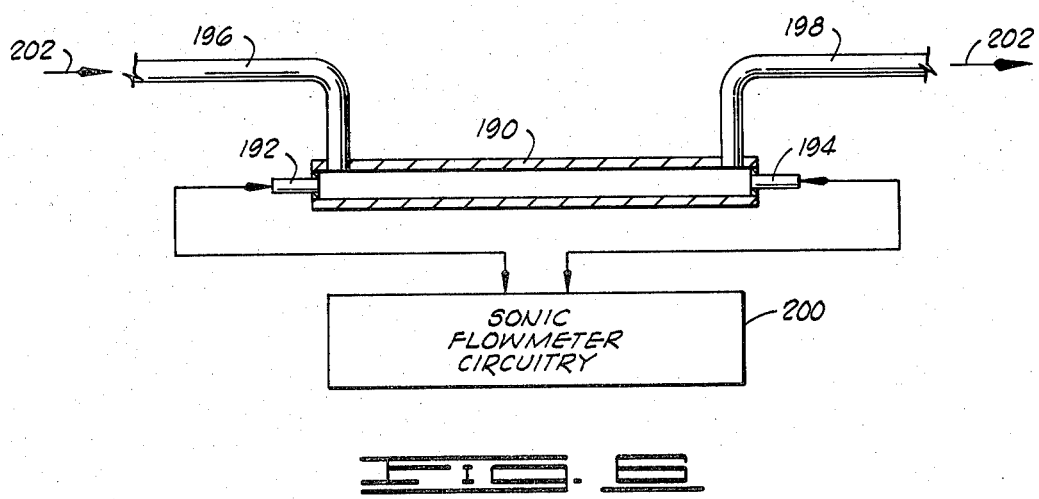
FIG. 6 illustrates one form of conduit array in combination with a sonic flowmeter wherein water separation is readily enabled.

When used, the mixing pipe section 14 may include a Koch mixer 20 followed by an assembly of straightening vanes 22 which are suitably secured to resist the force of fluid flow by means of conventional fasteners. The mixing element 20 will serve to mix the oil-water mixture prior to entry into the metering pipe section 16. However, when using an axial-type flowmeter, as shown in FIG. 6, sufficient mixing will result from the ells in the tubing connection, as will be described.

The metering pipe section 16 includes a frequency sensing and transmitting transducer 24 as located downstream and directed toward a counterpart frequency sensing and transmitting transducer 26, each of which provides electrical connection by respective leads 28 and 30 to sonic flowmeter 18. Threaded feedthrough fixtures 32 and 34 are secured diagonally and in-line across pipe metering section 16 to provide the requisite ultrasonic energy interaction. The sonic flowmeter 18, including the requisite frequency sensing and transmitting transducers, is a commercially available equipment which is obtainable from Mapco, Inc. of Tulsa, Okla.

An initiation pulse conducted from sonic flowmeter 18 triggers transmission of a sonic pulse from transducer 24 through the liquid in the pipe section 16 to transducer 26. Transducer 26 receives the sonic pulse and converts it back into electrical energy for conducting via connector 30 for input to sonic flowmeter 18 and subsequent electronic detection which generates yet another pulse to trigger transducer 24. The result is a continuous series of pulses traveling from transducer 24 to transducer 26, and the frequency of these pulses is essentially proportional to the velocity of sound between transducer 24 and transducer 26 traveling in the upstream direction relative to mixture flow. This constitutes a first frequency which may be designated as $F_B$.

On a shared time basis, a similar train of pulses is generated in the opposite direction with transducer 26 transmitting and transducer 24 receiving. This frequency, when detected and processed, is designated as frequency $F_A$ as derived for ultrasonic energy traveling downstream in the direction of transducer 24. It can be shown that when these upstream and downstream frequencies are subtracted one from the other, the following expression results:

$$V = f/K$$

where:
 V = flow velocity in the pipe line in distance per unit time;
 f = frequency difference in pulses per second which is equal to $F_A - F_B$; and
 K = a constant, which is directly proportional to pipe diameter and also a function of the specific electronic design and flow pipe section geometry.

Sonic flowmeter 18 provides a plurality of outputs 36, including raw frequency $F_A$ and $F_B$ outputs, via connections 38 and 40. The outputs 36 include individual output connections which provide the following data outputs to a digital computer 42. The outputs on cables 36 are: instantaneous flow rate in terms of frequency; output flow rate in terms of average frequency f as averaged over a preselected adjustable time period; an analog voltage output which varies in proportion to frequency f from 0 volts to +10 volts D-C and is indicative of flow rates; flow rate in the form of a calibrated analog current; indication of flow direction as between the upstream and downstream sources; malfunction analog light indication; and, indication of transmitted ultrasonic energy attenuation for further malfunction protection.

The outputs from sonic flowmeter 18 are used variously to determine output data and other system characteristics for analysis of the oil-water system. The frequencies $F_A$ and $F_B$ as output on connectors 38 and 40 are applied to frequency to voltage converters 44 and 46, respectively. The converters 44 and 46 provide frequency indicative analog voltage outputs via respective leads 48 and 50. Analog voltage outputs on leads 48 and 50 are then applied to a summing network 52 which provides input to a mean amplifier 54 providing analog output on lead 56 that indicates the mean or average analog value as between the $F_A$ and $F_B$ analog signals. The average analog voltage on lead 56 amounts to the average frequency as between $F_A$ and $F_B$ which is a signal proportional to the speed of sound in the oil-water medium.

The speed of sound voltage on lead 56 is then applied to an op-amp 58 functioning as a scaling circuit and including a zero or base calibrator feedback potentiometer 60. The scale output signal from op-amp 58 is then applied to a suitable form of recorder 62, a type which is well-known in the oil fields, and in geophysical and related arts. Recorder 62 may constitute any direct readout recorder such as inkpen, camera or the like, and such output may be further recorded on magnetic tape for storage or transmittal to a central laboratory for further processing. Additionally, meter readout may be provided on site for instantaneous monitoring.

Simultaneous with derivation of the speed of sound data is sensing and recording of the temperature of the flowing oil-water medium since the temperature of the flowing medium exhibits great effect on output data. Temperature may be sensed by suitable sensor attachment 64 providing input to a digital pyrometer 66 of a commercially available type. Analog output from pyrometer 66 may be directly applied to a suitable meter or other indicator 68 as well as to the recorder 62. Digital output in computer compatible binary decimal format may also be applied from digital pyrometer 64 directly to the digital computer 42.

Still other and more refined data output can be derived from utilizing the digital computer 42 in conjunction with sonic flowmeter 18 and temperature sensing structure. The computer 42 may be a well-known and commercially available type of minicomputer such as the Texas Instruments Model AES8000. Temperature output from pyrometer 66 is applied to computer 42 as is the output from op-amp 58 which may be passed through an analog digital converter 70 of conventional type in order to provide output in designated format for entry to computer 42. In like manner, or, alternatively, the plurality of outputs 36 constituting data outputs from sonic flowmeter 18 may be applied in like manner to computer 42 with permanent output provided on peripheral equipment, e.g., print-out 72 and/or recorder 74.

Further analog flow rate data may be derived by taking the analog voltage outputs on leads 48 and 50 for input to a difference amplifier 76. Amplifier 76 then derives an analog voltage output on lead 78 that is proportional to flow rate V which is then input to a scaler circuit 80 thereby to provide calibration in relative bounds for input via lead 82 to a remaining channel of recorder 62.

In order to enable actual water velocity measurement and therefore, self-calibration, a control valve 90 is included downstream from metering section 10. Control valve 90 is controllable to open or close fluid flow through downstream conduit 92 under control of a suitable form of timing circuit 94 that serves to periodically stop fluid flow for measurement of speed of sound in the existent water of the oil-water system. Insuring the separation of sufficient amounts of water will be further described below. The timing circuit 94 may be actuated in any of various well-known manners including a remote control 96, and corresponding input indication is provided by lead 98 to digital computer 42.

Initial calibration of the system of FIG. 1 depends upon the compilation and storage of data whereupon the system is then capable of electronic calibration for the particular type of water, oil and other related parameters. FIG. 2 illustrates a graph relating to pure water and kerosene of 42° API, i.e., relative specific gravity. The graph proceeds in terms of average frequency in KHz on ordinate Y versus temperature in °F. along abscissa X, and indications range from the pure water indicator line 100 to the 100% kerosene indicator line 102. Thus, the dash line 104 would indicate a transgression in terms of average frequency Y for a constant temperature X of 75° for an oil-water mixture range of from 100% water to 100% kerosene. The water line 100 has been linearized using regression analysis.

FIG. 3 illustrates some possible variations of water and other hydrocarbon liquids, such variations necessarily being accounted for in pre-calibration of the system of FIG. 1. Thus, there can be noted a considerable difference between curves 106 and 108, that of seawater and distilled water, respectively, and this points up the particular value of the present invention wherein actual water in the oil-water system is anlayzed separately for input of the calculation data. The remaining four curves represent other oil products of different weight and consistency ranging from line 100 Skelly crude oil "S" to line 112 Mobil regular gasoline. Each of the hydrocarbon products 110–112 illustrate additional differences of speed of sound in meters per second versus °C., and therefore the need for accurately calibrating the indicator system of FIG. 1 for each particular oil-water system.

The method of self-calibrating the sonic flowmeter for water cut determination can be carried out in several modes of operation which would allow the flowmeter to measure sonic energy speed in water only. In the case where the flow is at fairly high water cut, for example over 60% water, it would only be necessary to stop flow through the conduit for a time sufficient to allow separation of the oil at the top of the measurement cell with subsequent measurement of the sonic velocity in water only. Using the measurement cell 10 of FIG. 1, the cell 10 would be mounted in the fluid flow system in a downward offset from the primary flow line so that water only can be collected during brief stoppage of flow by means of control valve 90 in response to timing circuit 94. The requisite timing data indicating flow stop and water measurement is input via connection 98 to digital computer 42 to enable proper input of the water data for final calculation of water cut in the flowing oil-water system.

Figure 4:
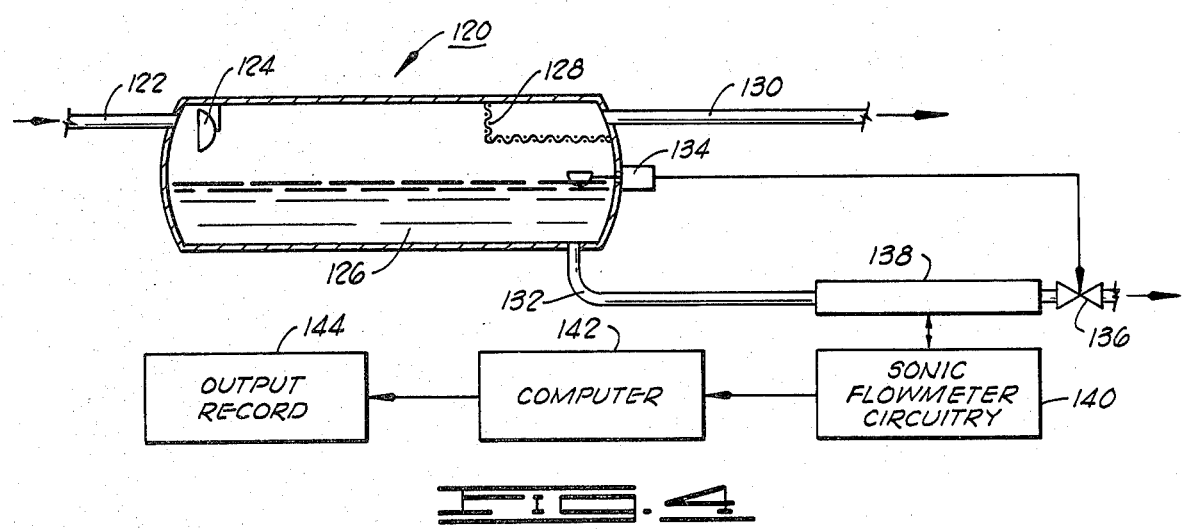
FIG. 4 is an idealized block diagram of the sonic flowmeter of the present invention as utilized with a two phase separator.

In an alternative system, the flowmeter can be placed on the dump of a two phase separator 120 as is shown in FIG. 4. Thus, a standard type of two phase separator 120 consists of the input liquid line 122 in alignment with a baffle 124 to promote the separation of liquid and gas, and thereby to retain residual fluid 126 therein. A mist extractor 128 allows vapor phase output via conduit 130, and liquid output is via conduit 132 as controlled in conventional manner by a float control 134 actuating a control valve 136. Fluid output from separator 120 may then be passed through a measurement cell 138 and the associated sonic flowmeter circuitry 140, such as is illustrated in FIG. 1. Sound velocities of water as well as the oil-water mixture are then input to a computer 142 with final output being presented by record 144 or similar indicating structure.

When the sonic flowmeter circuitry 140 and measurement cell 138 are placed on the dump of two phase separator 120, as it uses a snap-action level controller, flow can be stopped during the early part of a dump to enable measurement of speed of sound in the particular water of the system. As the water comes out of the separator 120 first, it is only necessary to allow flow of enough water to flush the measurement cell 138, on the order of a few seconds, whereupon flow can be stopped to trap the water within measurement cell 138 for a brief interval during which sonic flowmeter circuitry 140 obtains the water data for input to computer 142. The water measurement operation can be manual or time programmed and can be done once during the test of each particular well, once each day or other period of time, or on each separator dump. In any event, after a brief water measurement interval, the system recommences function as a measurement cell for flowing oil-water fluid with the speed of sound and water data already entered in calibration to computer 142.

Figure 5:
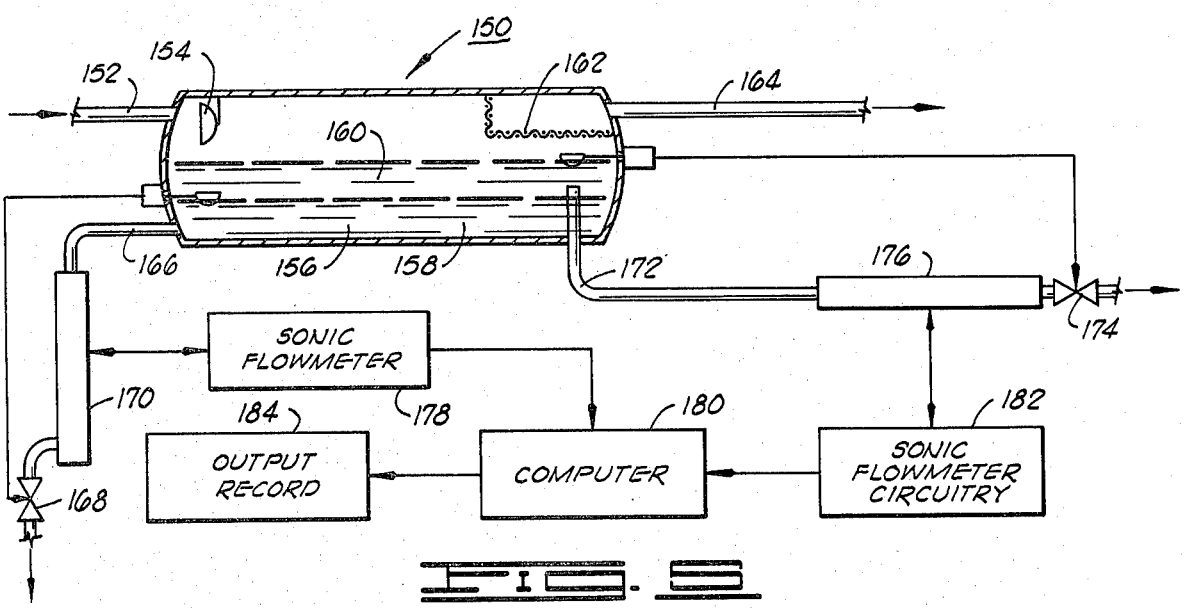
FIG. 5 is an idealized block diagram of the improved sonic flowmeter as utilized with a three phase separator.

FIG. 5 depicts a three phase separator 150 which may be used in various ways to provide the velocity of sound in water information. Three phase separator 150 includes the incoming fluid conduit 152 having a centrifugal separator 154, or other suitable baffling, enabling liquid deposit 156, the water deposit 158 underlying the oil 160. Once again, you have the mist extractor 162 and vapor phase output conduit 164, but tapping and release of the separator 150 are carried out in two distinct operations. Water output is carried out by conduit 166 and float-controlled valve 168 to a measurement cell 170. Oil output (and some water), the floating component 160, is effected through conduit 172 leading to a measurement cell 176 and the float controlled valve 174. Thus, the speed of sound of water in the system and water flow rate can be measured by measurement cell 170 and sonic flowmeter 178 with direct input of well water data to the computer 180. Water cut of the output oil-water system may then be measured during oil dumps by measurement cell 176 and flowmeter circuitry 182 with requisite input supplied to the computer 180. Water cut of the total stream entering the system can be determined by a totalizing function in computer 180, totalizing flow rate, through measurement cells 176 and 170 as determined by sonic flowmeters 182 and 178 inputting thereto. Computer output of the oil-water flow data is then apparent at output record 184. The float controlled valve 174 can be easily adjusted so that all emulsions are included in the oil dumps through measurement cell 176.

FIG. 6 illustrates an axial type flow measurement cell 190 wherein the upstream and downstream transducers 192 and 194, respectively, are disposed to view axially through the cell. Such measurement cells are commercially available for liquid sonic speed measurement from various suppliers, e.g., the aforementioned Mapco, Inc. The axial-type flowmeter is also especially desirable for self-calibration application since it does not require pre-mixing stages in the flow conduit. The measurement cell 190 can receive input flow via conduit 196 with flow output proceeding through conduit 198, and the sonic flowmeter circuitry 200 then functions with transducers 192 and 194 in the same manner as described relative to FIG. 1. It may be noted, however, that the measurement cell 190 is installed at a downward offset from the primary conduit direction 202 and serves to aid in separation of oil and water when flow is stopped. That is, since the oil is the lighter component it will seek a higher gravitational level within the system, and in cases of appreciable water content it will leave the measurement cell 190 completely filled with water. Measurement cell 190 of FIG. 6 can of course be used with any of the aforedescribed systems to carry out its measurement function, and any mixing or straightening components, if required, may be included within input conduit 196.

When utilizing an axial flow cell, stoppage of flow in a system having high water cut will result in separation sufficient that measurement can be made through the water beneath a layer of oil floating to the top of the cell. However, installation of the measurement cell at a downward oriented offset enhances separation still further. In addition, there are many other installation configurations which can contribute to the oil-water separation. Thus, still further enhancement may result from installation of the measurement cell 190 at a slight angle of inclination rather than horizontal, e.g., with measurement cell 190 mounted at an angle of 10° relative to primary flow direction as indicated by arrow 202. Still other geometric considerations of measurement cell installation such as vertical mounting relative to primary flow direction 202, offset vertical mounting and the like will serve to enhance water cut measurement during flow stoppage. Many different installation possibilities exist and these will depend on flow characteristics of particular wells and the separator and flow facilities at particular sites.

The foregoing discloses a novel method for self-calibrating sonic velocity type water cut metering systems. The inclusion of means whereby water phase only is periodically measured for input calibration to the final computation stages of the flowmeter circuitry serves to enable determination of oil-water percentages to greater accuracy and reliability.

Changes may be made in the combination and arrangement of elements as heretofore set forth in the specification and shown in the drawings; it being understood that changes may be made in the embodiments disclosed without departing from the spirit and scope of the invention as defined in the following claims.

What is claimed is:

1. A method for self-calibrating a system for determining quantitative and volumetric data of an oil-water mixture flowing in a conduit, comprising the steps of:
   providing in said conduit a metering section for controlled entrapment of water only;
   offsetting said metering section below said conduit so that stoppage of the oil-water mixture flow causes liquid separation thereby to enhance water only presence in said metering section;
   deriving by sonic flowmeter the speed of sonic energy transmitted through said metering section when containing water only;
   deriving by sonic flowmeter the speed of sonic energy transmitted through said metering section when containing said oil-water mixture; and
   determining said quantitative and volumetric data of said oil-water mixture, said determination being based upon said speed of sonic energy through said metering section when containing said oil-water mixture and upon a calibration adjustment dependent upon said speed of sonic energy through said metering section when containing water only.

2. A method as set forth in claim 1 wherein:
   said sonic flowmeter transmits and receives axially through said metering section.

3. A method as set forth in claim 1 wherein:
   said conduit is the liquid dump output from a two-phase separator tank wherein initial output flow of a dump is water only for a period of derivation of the speed of sonic energy.

4. A method as set forth in claim 3 wherein:
   said sonic flowmeter transmits and receives axially through said metering section.

5. A method as set forth in claim 1 which further comprises:
   initially charging said metering section with water of said oil-water mixture for a duration to enable derivation of the speed of sonic energy therethrough.

6. A method for self-calibrating a system for determining quantitative and volumetric data of an oil-water mixture flowing from a three phase separator tank having a water dump conduit and an oil dump conduit, said method comprising the steps of:
   placing a water metering section in the water dump conduit of said tank;
   placing a second metering section in the oil dump conduit of said tank;
   deriving by sonic flowmeter the speed of sonic energy transmitted through said water metering section during water dumps;
   deriving by sonic flowmeter the speed of sonic energy transmitted through said second metering section during oil dumps;

determining volumetric data of said water flowing through said water metering section during said water dumps;

determining quantitative and volumetric data of an oil-water mixture flowing through said second metering section during said oil dumps, said determination being based upon said speed of sonic energy transmitted through said second metering section during said oil dumps and upon a calibration adjustment dependent upon said speed of sonic energy transmitted through said water metering section during said water dumps; and totalizing the data determined for said water metering section and said second metering section to determine the watercut of the total oil/water system.

7. A method as set forth in claim 6, wherein:
said sonic flowmeters are aligned to transmit and receive axially through said water metering and second metering sections.

8. A method as set forth in claim 7 wherein:
said water metering section is laterally offset relative to the axis of its associated main flow conduit thereby to enhance liquid separation within the water metering section.

9. In apparatus for determining quantitative and volumetric data of an oil-water mixture flowing in a conduit, the improvement comprising:

a metering section disposed in said conduit laterally offset from the main axis of said conduit;

sonic flowmeter means, disposed generally axially in said metering section, for measuring the speed of sound in a liquid flowing therethrough; and means for periodically stopping flow of liquid through said metering section for a duration sufficient to allow oil and water separation.

10. Apparatus as set forth in claim 9 which is further characterized in that:
said metering section is laterally offset below a generally horizontal conduit.

11. Apparatus as set forth in claim 9 which is further characterized in that:
said metering section is aligned at a slight angle relative to the axis of the conduit.

12. In combination with a two-phase separator tank having a dump conduit for outputting an oil-water mixture, apparatus comprising:

a metering section disposed in said dump conduit;

sonic flowmeter means, disposed generally axially in said metering section, for deriving the speed of sound in a liquid flowing therethrough;

means for periodically stopping flow of liquid through said metering section for a duration sufficient to allow derivation of the speed of sound in water only; and computation means receiving input data representing the speed of sound in water only and the speed of sound in the oil-water mixture to generate output data for volume of oil and water in the flowing mixture per unit time.

13. Apparatus as set forth in claim 12 which is further characterized in that:
said metering section is laterally offset from said dump conduit to enhance the separation of oil and water during liquid flow stoppage.

14. In combination with a three-phase separator tank having a water dump first conduit and an oil-water dump second conduit for outputting collected oil-water mixture, apparatus comprising:

a first metering section disposed in said first conduit;

sonic flowmeter means, disposed generally axially in said first metering section, for generating first speed of sound data output representing the speed of sound in water flowing therethrough;

a second metering section disposed in said second conduit;

second sonic flowmeter means, disposed generally axially in said second metering section, for generating second speed of sound data representing the speed of sound in the oil-water mixture flowing therethrough; and computation means receiving said first and second speed of sound data and generating output indication of the total volume of oil and water flowing through said three-phase separator tank.

* * * * *